United States Patent [19]

Lindley et al.

[11] Patent Number: 5,185,469

[45] Date of Patent: * Feb. 9, 1993

[54] PROCESS FOR ACYLATION OR ALKYLATION OF AROMATIC COMPOUNDS IN HYDROGEN FLUORIDE

[75] Inventors: Daniel D. Lindley, Portland; Timothy R. Ryan, Corpus Christi, both of Tex.; Thomas A. Curtis, Tega Cay, S.C.; Edward M. De la Garza, Corpus Christi, Tex.; Charles R. Hilton, North Kingstown, R.I.; Thomas M. Kenesson, Corpus Christi, Tex.

[73] Assignee: Hoechst Celanese Corp., Somerville, N.J.

[*] Notice: The portion of the term of this patent subsequent to Nov. 26, 2008 has been disclaimed.

[21] Appl. No.: 748,171

[22] Filed: Aug. 23, 1991

Related U.S. Application Data

[63] Continuation-in-part of Ser. No. 593,143, Oct. 5, 1990, Pat. No. 5,068,448, which is a continuation-in-part of Ser. No. 445,055, Dec. 4, 1989, Pat. No. 4,990,681.

[51] Int. Cl.$^5$ ............................................... C07C 45/45
[52] U.S. Cl. .................................... 568/319; 568/323
[58] Field of Search ................................ 568/319, 323

[56] References Cited

U.S. PATENT DOCUMENTS

| 3,385,886 | 5/1968 | Nicholson et al. | 260/515 |
| 4,981,995 | 1/1991 | Elango et al. | 562/406 |
| 4,990,681 | 2/1991 | Curtis et al. | 568/324 |
| 5,068,448 | 11/1991 | Lindley et al. | 568/319 |

FOREIGN PATENT DOCUMENTS 57-188343 9/1985 Japan.

OTHER PUBLICATIONS

Dolkady Akademii Nauk USSR, 95(2), 297–299 (1954).
Baddely et al., Journal of the Chemical Society, 4943–4945 (1956).
Zhurnal Fizicheskoi Khimii, 31, 1377–1386 (1957).

*Primary Examiner*—James H. Reamer
*Attorney, Agent, or Firm*—James M. Hunter, Jr.

[57] ABSTRACT

A continuous process is disclosed for the acylation or alkylation of aromatic compounds in hydrogen fluoride. The aromatic compound is sufficiently insoluble in hydrogen fluoride that a two phase reaction medium forms. However, surprisingly, the product acylated or alkylated aromatic compound is soluble in hydrogen fluoride. The present invention particularly relates to use of a continuous, multi-stage process for carrying out the acylation or alkylation reaction. In the multi-stage process, the continuous phase can be either the hydrogen-fluoride rich phase or the aromatic compound-rich phase. The movement of the continuous phase relative to the non-continuous (dispersed) phase can be counter-current or concurrent. The multi-stage process can be operated in a manner such that the aromatic compound feed to the reaction is entirely consumed or such that unreacted aromatic compound is recycled.

6 Claims, 2 Drawing Sheets

PROCESS FOR ACYLATION OR ALKYLATION OF AROMATIC COMPOUNDS IN HYDROGEN FLUORIDE

This application is a continuation-in-part of pending application Ser. No. 07/593,143, filed Oct. 5, 1990, U.S. Pat. No. 5,068,448 which is a continuation-in-part of Ser. No. 445,055, filed Dec. 4, 1989, now U.S. Pat. No. 4,990,681, issued Feb. 5, 1991.

BACKGROUND OF THE INVENTION

1. Field of the Invention

The present invention relates to the acylation or alkylation of aromatic compounds in hydrogen fluoride, wherein the acylated or alkylated product is soluble in hydrogen fluoride but the aromatic compound is sufficiently insoluble in hydrogen fluoride that a two phase reaction medium forms. The present invention particularly relates to a continuous multistage process for carrying out the acylation or alkylation of aromatic compounds in hydrogen fluoride.

2. Description of Related Art

The following information is disclosed in accordance with the terms of 37 CFR 1.56, 1.97 and 1.98.

U.S. Pat. No. 3,385,886, shows the production of phenylalkane derivatives such as ibuprofen in which the first step of the process is the reaction of phenylalkane with acetyl chloride in the presence of aluminum chloride to produce an alkylphenylacetophenone.

Japanese Patent Publication (Early Disclosure) No. 60 [1985]188,343, discloses the preparation of p-isobutylacetophenone by the acetylation of isobutylbenzene using an acetylating agent acetyl fluoride prepared by reacting acetic anhydride with hydrogen fluoride, and as a catalyst, a combination of hydrogen fluoride and boron trifluoride.

Baddely et al., Journal of the Chemical Society, 4943-4945 [1956], discloses on page 4945 the preparation of 4'-isobutylacetophenone by the Friedel-Crafts acetylation of isobutylbenzene with acetyl chloride using aluminum chloride as a catalyst.

U.S. Pat. No. 4,981,995, issued Jan. 1, 1991 to Elango et al., shows the production of 4'-isobutylacetophenone (IBAP) by the Friedel-Crafts acetylation of isobutylbenzene (IBB) with an acetylating agent which may be acetyl fluoride (AcF) or acetic anhydride ($Ac_2O$), using a catalyst which may be hydrogen fluoride. The 4'-isobutylacetophenone is disclosed as an intermediate in a process for the production of ibuprofen.

U.S. Pat. No. 4,990,681 issued Feb. 5, 1991, discloses the operation of an extractor-reactor to produce IBAP and the removal of HF from the IBAP product by reacting the HF with acetic anhydride in an HF removal column, both contemplated to be used in combination with the process of the present invention. The entire disclosure of U.S. Pat. No. 4,990,681 is hereby incorporated by reference herein.

The acylation or alkylation of aromatic compounds in hydrogen fluoride is well known in the art. Since, typically, the aromatic compound reactant has a limited solubility in hydrogen fluoride, whereby the contact between the aromatic compound and the acylating or alkylating agent is restricted, the rate of the reaction is reduced. In the past, due to the reduced rate of reaction, the acylation or alkylation of aromatic compounds in hydrogen fluoride was carried out in a batch mode, typically in a continuously stirred batch reactor.

Examples of aromatic compounds which form a separate and distinct phase with hydrogen fluoride are described in Dolkady Akademii Nauk USSR, 95(2), 297-299 (1954) and Zhurnal Fizicheskoi Khimii, 31, 1377-1386 (1957). Aromatics sparingly soluble in hydrogen fluoride (approximately one (1)% by weight or less) include naphthalene, phantrene, diphenylmethane, triphenylmethane, chlorobenzene, tetralin, 2-methylnaphthalene, and diphenyl. Many aromatics, especially those with—H or—alkyl substitution are often sparingly soluble in hydrogen fluoride. Thus, one skilled in the art can understand the broad applicability and considerable value of a reaction technique which would permit the continuous acylation or alkylation of aromatic compounds in hydrogen fluoride.

SUMMARY OF THE INVENTION

In accordance with the present invention, a continuous process is provided for acylating or alkylating an aromatic compound in hydrogen fluoride, wherein the aromatic compound has a sufficiently limited solubility in hydrogen fluoride that a two phase reaction system is formed. The continuous process is carried out countercurrently or concurrently in a multistage reactor. The continuous phase during the reaction contacting period can be either the aromatic compound-comprising phase or the hydrogen fluoride-comprising phase. The present process is particularly advantageous in that hydrogen fluoride serves at least a triple function, as catalyst, reaction medium (solvent), and (surprisingly) as extractant for the acylation or alkylation product of the aromatic compound. In addition, depending on the acylating agent utilized, in acylation reactions, the hydrogen fluoride can serve as a component of the acylating agent.

The process of the present invention comprises a continuous process for the acylation or alkylation of aromatic compounds in hydrogen fluoride, said process comprising the steps of:

a) feeding liquid hydrogen fluoride and at least one acylation agent or at least one alkylation agent into an extractor-reactor to form a first, hydrogen fluoride-rich phase;

b) feeding an aromatic compound-comprising material into said extractor-reactor to form a second, aromatic compound-rich phase; and c) contacting said first, hydrogen fluoride-rich phase with said second, aromatic compound-rich phase in a manner, within said extractor reactor, such that said acylation agent or said alkylation agent reacts with said aromatic compound to form an acylation product or an alkylation product of said aromatic compound which is extracted into said hydrogen fluoride-rich phase.

For purposes of illustration, the process of the present invention is first described in detail in terms of the production of 4'-isobutylacetophenone (IBAP) by the Friedel-Crafts acetylation of isobutylbenzene (IBB) with an acylating (acetylating) agent which can be acetyl fluoride (AcF) acetic anhydride, acetic acid, or mixtures thereof, in hydrogen fluoride catalyst/solvent. Subsequently, the process is described in terms of the acylation and alkylation of other aromatic compounds which also have limited solubility in hydrogen fluoride.

In accordance with the present invention, IBAP is produced in a continuous process wherein IBB is reacted with an acetylating agent in the presence of liquid HF as a catalyst/solvent, in a multi-stage reactor, for example, an unitary extractor-reactor.

In one embodiment of the present invention, wherein the hydrogen fluoride (HF)-comprising phase is the continuous phase in the reaction system, IBB which is lighter than and substantially insoluble in HF, forms an IBB-rich phase, e.g., as droplets, which percolates upwardly through an HF-rich phase containing the acetylating agent. The formed IBAP is selectively soluble in and is extracted into the HF-rich phase, while the bulk of unreacted IBB is withdrawn and externally recycled to the extractor-reactor with a fresh supply of IBB. The recycled IBB may be further purified prior to feeding it back to the extractor-reactor. A product stream withdrawn from the vessel comprises IBAP, HF, a small amount of IBB, and in many cases, varying amounts of acetic acid and acetyl fluoride, the specific amounts of these components depending, among other factors, on the nature of the acetylating agent initially added. As used in this specification, the terms "feed point" or "point of withdrawal" may mean one or more points in the extractor-reactor at which the designated stream is fed or withdrawn.

Because IBB is slightly soluble in the HF-rich phase, that portion of such phase below the feed point of fresh and recycled IBB will often contain a small amount of IBB. Since this amount could be economically important, it is another aspect of this invention to provide additional residence time between the feed point of IBB and point of withdrawal of the product stream, i.e., a "finishing zone," such that a significant proportion of the IBB dissolved in the HF-rich phase has an opportunity to react with acetylating agent remaining in such phase to produce an additional amount of IBAP. Such finishing zone may be, for example, the bottom portion, below the IBB feed point, of the extractor-reactor vessel which contains only an HF-rich phase with dissolved IBB in the absence of any substantial amount of IBB-rich phase. Alternatively, or in addition to the foregoing expedient, the product stream may be transferred to and held in a separate vessel as the finishing zone, i.e., a "finishing reactor," for a period and under conditions to obtain further acetylation of dissolved IBB in a homogeneous system.

In accordance with another aspect of the invention, the operation of the extractor-reactor described previously is combined in an integrated process with the operation of an HF removal column utilizing acetic anhydride (Ac$_2$O) to react with the HF in the IBAP/HF and acetic acid/HF complexes present in the product of the extractor-reactor, forming acetyl fluoride (AcF) which together with free liberated HF is withdrawn as an overhead stream, with at least part of such stream being recycled to the extractor-reactor. The bottoms stream from the HF-removal column comprises IBAP and acetic acid (HOAc) at least some of which acid is produced in the foregoing reaction.

In accordance with still another aspect of the invention, the bottom stream from the HF removal column is fed to a light ends column where the bulk of the acetic acid is separated from the IBAP, with at least part of the acetic acid being recycled to the extractor-reactor.

In another embodiment of the present invention, the extractor-reactor can be operated in a manner such that the discontinuous phase exists only throughout a portion of the length of the reactor, eliminating the need to recycle discontinuous phase material. In this latter embodiment, the feed rate of the reactant, which comprises the discontinuous phase, is limited to that which is reacted/dissolved in the continuous phase prior to exit of the continuous phase from the extractor-reactor. It is preferable to use this embodiment of the present invention when the aromatic compound to be acylated or alkylated is unstable in the HF-comprising phase of the reaction medium and thus, contact time should be limited.

DESCRIPTION OF THE PREFERRED EMBODIMENTS

Figure 1:
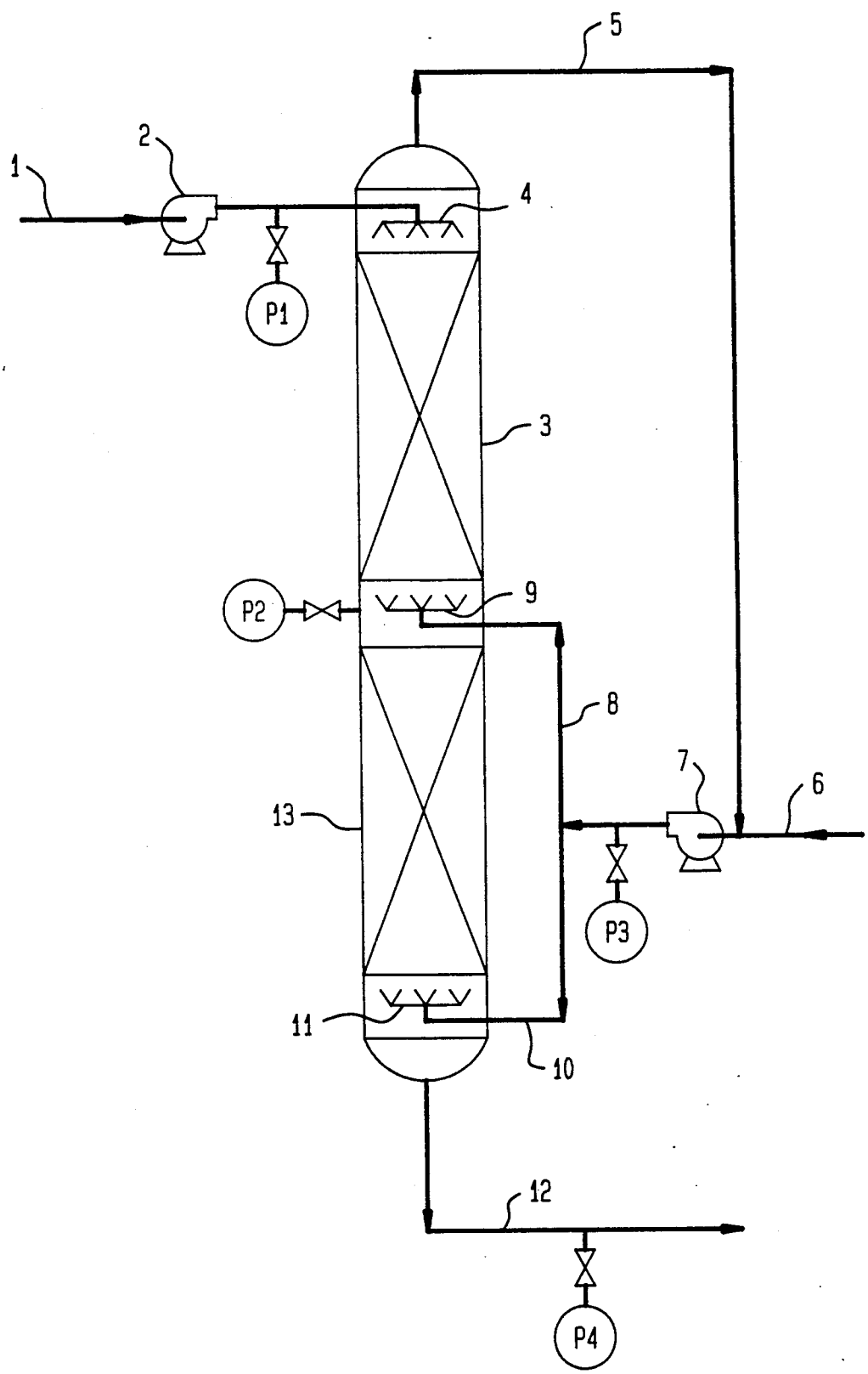
FIG. 1 is a schematic diagram of a process for acylation or alkylation of aromatic compounds in hydrogen fluoride using an extractor-reactor and optional finishing zone contemplated under this invention.

The first illustration of the process of this invention, wherein 4'-isobutylacetophenone (IBAP) is produced by the Friedel-Crafts acetylation of isobutylbenzene (IBB), is shown in the following equation:

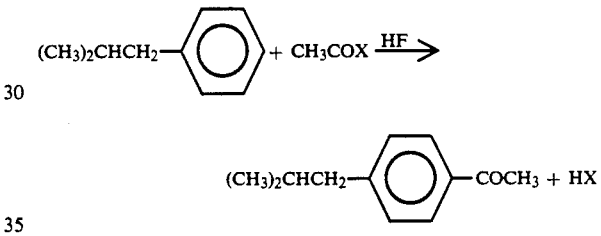

where "X" is the residue, minus the acetyl group, of an effective acetylating agent. Acetylating agents which may be used are, for example, acetyl fluoride (X=F), acetic anhydride (X=—OCOCH$_3$) and acetic acid (X=—OH). Mixtures of acetylating agents may also be used, and form in situ if certain acetylating agents such as acetic anhydride, are used. The acetic anhydride reacts with IBB to form IBAP and acetic acid which is also an acetylating agent. Moreover, acetic anhydride also reacts with HF to form acetyl fluoride, another acetylating agent, and acetic acid. If free acetic acid is used as all or part of the acetylating agent, some of its anhydride can be, and preferably is, added to further react with the water of reaction. Alternatively, acetyl fluoride, if present, will also react with water of reaction to form HF and acetic acid. The product of the reaction thus comprises IBAP and HF and/or free acetic acid, with HF being present in appreciable amount in either case because of the large excess used as solvent/-extractant/catalyst, e.g., about 7 to about 80 moles per mole of IBB/IBAP. The recycle ratio, i.e., the ratio of the weight of IBB-rich phase being recycled from at or near the top to the IBB feed point, preferably below the feed point of HF and acetylating agent in the reactor, to the total weight of material entering or leaving the reactor at steady state, may be in the range, for example, of about 2 to about 0.03, preferably about 0.5 to about 0.1. The use of packing in the extractor-reactor is beneficial in that it increases the efficiency of HF-rich phase/IBB-rich phase contact and helps to provide "plug flow" of the IBB-rich phase, which is preferably the discontinuous phase, through the HF-rich phase, which is preferably the continuous phase. The reaction may be carried out a temperature, for example, of about 45° C. to about 80° C., at a pressure which prevents boiling; for example, a pressure of about 35 psig to about 150 psig over a residence time of, for example, about 0.3 hours to about 4 hours.

As stated, the product of the extractor-reactor may pass through a finishing zone of the extractor-reactor or may be sent to a separate finishing reactor to maximize the homogeneous phase conversion of IBB to IBAP. Such finishing zone or reactor may be operated at a temperature and pressure similar to those of the extractor-reactor and, for a residence time, for example, of about 0.1 hours to about 4 hours, preferably about 0.5 hours to about 2 hours. The finishing zone or reactor can be used in a plug flow arrangement (by packing the reactor) or in a laminar flow arrangement.

The product stream withdrawn from the extractor-reactor or the finishing reactor contains free, i.e., substantially uncomplexed HF, and HF which is complexed with IBAP and, acetyl fluoride if acetic anhydride or acetic acid is used as all or part of the acetylating agent. The product stream also contains HF, water and/or acetic acid respectively, formed as a byproduct of the acetylation reaction. Some of the acetic acid present also tends to form a complex with HF. Additionally, the product stream may also contain unreacted isobutylbenzene (IBB), acetyl fluoride (AcF), acetic acid (HOAc) and acetic anhydride (Ac₂O), depending on the extent of the reaction or initial stoichiometric ratios employed.

To separate both the uncomplexed and complexed HF from the IBAP and acetic acid in the product stream from the extractor-reactor, such stream may be sent to an HF-removal column, the operation of which is disclosed in U.S. Pat. No. 4,990,681, the entire disclosure of which has previously been incorporated by reference. In such operation, acetic anhydride (Ac₂O) is added to the column below the feed point of the entering stream (which comprises aromatic ketone and HF) and reacts with the complexed HF to form acetyl fluoride (AcF) and acetic acid (HOAc) as shown in the following equation:

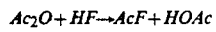

$$Ac_2O + HF \rightarrow AcF + HOAc$$

The acetyl fluoride is relatively volatile and is withdrawn from the top of the column with the initially uncomplexed HF, which is separated and rises from the entering stream at or near its feed point. Some IBB, if present, can also be collected overhead for recycle back to the reactor. A less volatile stream comprising IBAP and acetic acid is withdrawn from the bottom the column. The reaction and stripping operations occurring in the HF-removal column may be carried out at a temperature, for example of about 30° C. to about 155° C. and a pressure, for example, of about 0 psig to about 25 psig.

To further purify the desired IBAP product and partially recover some of the acetyl values of the system, the bottom stream from the HF-removal column may be sent to a light ends column where IBAP and heavier components leaving the bottom of the column are separated from acetic acid which leaves the top of the column and part of which may be recycled to the extractor-reactor where it may serve as part of the acetylating agent. The light ends column may be operated using a bottoms temperature, for example, of about 160° C. to about 200° C. and a pressure of about 30 mm Hg to about 110 mm Hg. If desired, the bottom stream from the light ends column may be sent to a heavy ends column where the IBAP is further purified by removal of most of the heavier impurities with which it is mixed in such bottom stream.

Referring now to FIG. 1, a stream comprising a mixture of liquid HF and acetylating agent entering the system through line 1 is continuously sent by pump 2 into extractor-reactor 3 where it is ejected as several streams from multi-opening liquid distributor 4 below a light IBB-rich phase collected at the top of the extractor-reactor 3. The mixture comprising HF and acetylating agent forms a dense, preferably continuous HF-rich phase traveling downwardly through extractor-reactor 3. IBB-rich light phase is withdrawn from the top of extractor-reactor 3 and flows through line 5 as an IBB recycle stream. Fresh IBB flows from a makeup source through line 6 where it is combined with the IBB recycle stream from line 5. By means of a valve adjustment (not shown), the combined IBB feed is propelled by pump 7 through line 8 and thence into the middle of extractor-reactor 3 through multiopening liquid distributor 9. In the alternative, if a separate finishing reactor (not shown) is employed, combined IBB feed may enter through line 10 and into the bottom of extractor-reactor 3 through multi-opening liquid distributor 11. In either case, in the preferred embodiment of the invention shown in FIG. 1, the IBB feed stream forms a discontinuous light IBB-rich phase which percolates upwardly through the continuous, dense HF-rich phase. As it does so, IBB reacts with acetylating agent to form IBAP, HF, H₂O and/or acetic acid by-product (as explained previously) which are absorbed into the continuous dense HF-rich phase. Such dense phase containing IBAP, HF, and in most cases, some acetic acid and AcF is withdrawn as reactor product through line 12. Some of the discontinuous light IBB-rich phase containing unreacted IBB collects at the top of extractor-reactor 3 and is recycled through line 5 as previously described.

In addition to reacting with acetylating agent in the continuous, dense HF-rich phase to form IBAP, some of the IBB in the discontinuous light IBB-rich phase remains unreacted and dissolves in the dense HF-rich phase which may therefore contain on the order of about 1 to 10 wt. % of dissolved IBB. If the IBB feed stream enters extractor-reactor 3 at its center through line 8 and liquid distributor 9, an HF-rich liquid containing acetylating agent and some dissolved IBB moves downward from liquid distributor 9 to the bottom of extractor-reactor 3 where the reactor product is withdrawn through line 12. This provides residence time for a portion of the dissolved IBB to further react with acetylating agent in a homogeneous system to form additional IBAP. In view of this operation, the lower portion of extractor-reactor 3 indicated in FIG. 1 by numeral 13, may be termed a "finishing zone." As stated, the same reaction may be carried out in a "finishing reactor" which is a vessel entirely separated from the extractor-reactor.

The designations P1, P2, P3 and P4 in FIG. 1 indicate primary sample points from which samples may be periodically withdrawn and analyzed.

Figure 2:
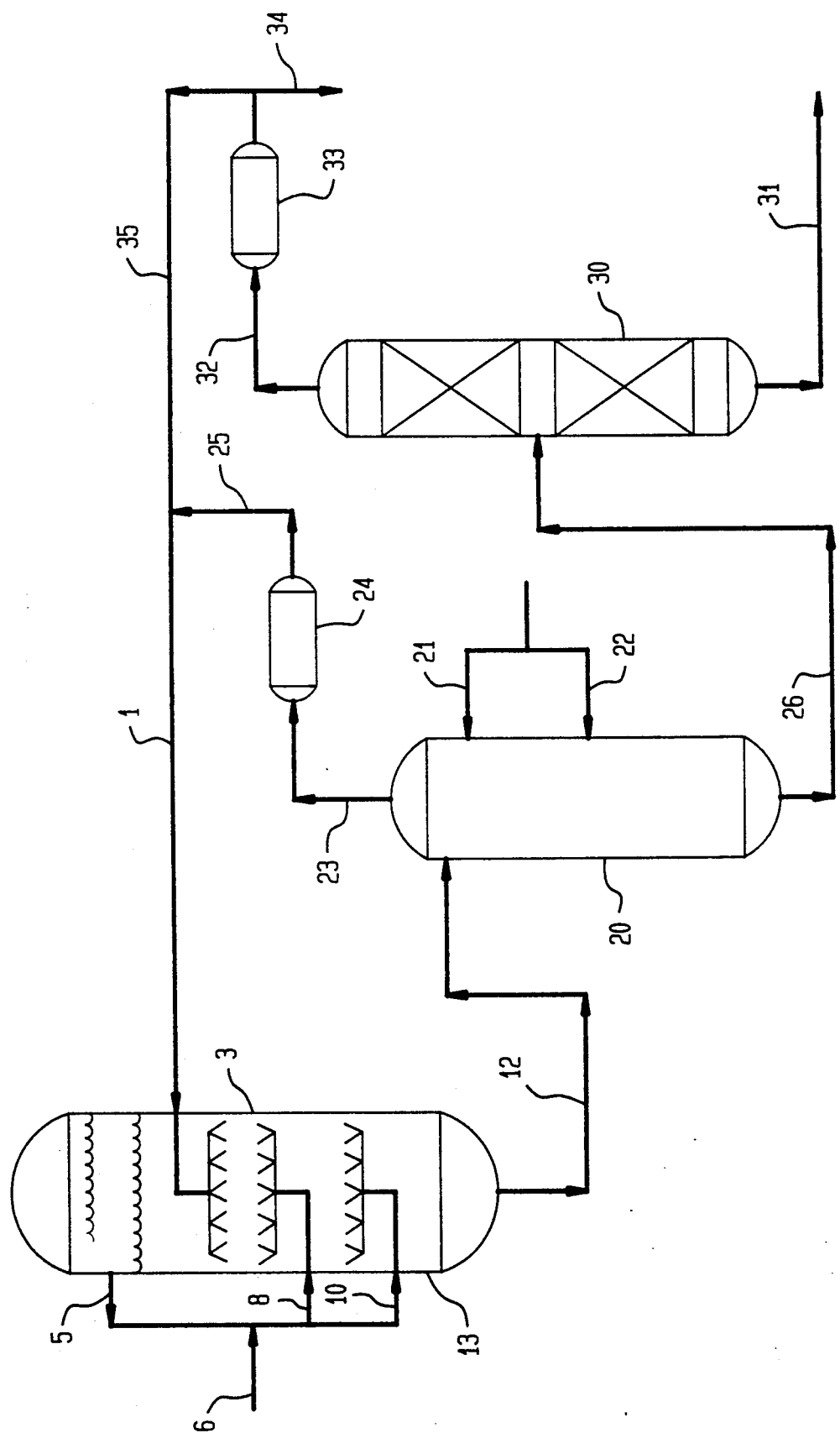
FIG. 2 is a schematic diagram of an integrated process for acylation or alkylation of aromatic compounds in hydrogen fluoride using an extractor-reactor having an optional finishing zone, an HF removal column, and a light ends column, in accordance with this invention.

Referring now to FIG. 2, the operation of extractor-reactor 3 is carried out as indicated in the description of FIG. 1 with the IBB feed stream fed to the middle or the bottom of extractor-reactor 3, and with the acetylating agent dissolved in liquid HF, entering extractor-reactor 3 through line 1, being a mixture of acetyl fluoride and, in most cases, acetic acid obtained as recycle streams from HF-removal column 20 and, possibly, light ends column 30. The composition of HF-acetylating mixture in line 1 is such that the mole ratio of HOAc:AcF ranges from about 0:1 to about 2:1, with the more preferred mole ratio of HOAc:AcF ranging from about 0.25:1 to about 2:1, and the most preferred mole ratio of HOAc:AcF ranging from about 0.65:1 to about 1.3:1. The HF content of the mixture is varied as necessary. Typically, the mole ratio of (HOAc+AcF) to HF ranges from about 1:5 to about 1:25, with a preferred mole ratio of (HOAc +AcF) to HF ranging from about 1:10 to about 1:20.

Reactor product from the bottom of extractor-reactor 3 comprising IBAP, HF, AcF, and HOAc, with all or most of the IBAP complexed with HF, is transported as feed to the top of HF-removal column through line 12. Acetic anhydride is injected into column 20 through two lines, line 21 slightly below the point of entry of the feed stream in line 12, and/or line 22 lower down the column, in sufficient quantity to react with substantially all the HF complexed with IBAP or acetic acid, as shown in U.S. Pat. No. 4,990,681. The products of this reaction are AcF and additional HOAc. Free and liberated HF, AcF and HOAc, as well as portion of unreacted IBB, are withdrawn from column 20 as an overhead stream through line 23, and, after passing through condenser 24, are recycled to extractor-reactor 3 through lines 25 and 1. In the alternative, the column can be operated such that the overload stream through line 23 comprises only HF and AcF, with all of the HOAc being withdrawn as part of a bottom stream comprising IBAP and HOAc. Such bottom stream is withdrawn through line 26 and flows to light ends column 30, where it is separated into a bottom stream composed largely of IBAP which is withdrawn through line 31, and an overhead stream composed largely of HOAc withdrawn through line 32. The IBAP-containing bottom stream 31 may be sent to a heavy ends column (not shown) for the removal of impurities less volatile than IBAP, and the IBAP may also be subjected to other purification treatments before being further utilized. The overhead HOAc-containing stream 32 from column 30 is condensed in condenser 33 and can be recycled as stream 35 to extractor-reactor 3 in combination with condensed overhead stream 25 from HF-removal column 20, as the feed through line 1 previously described. Any remainder of the HOAc-containing stream from light ends column 30 is withdrawn from the system through line 34.

The following examples further illustrate the invention.

EXAMPLE 1

An extractor-reactor 3 constructed from 20 ft. of 8" pipe was packed in two sections with ⅝" pall rings, as shown in FIG. 1. The reactor was maintained at 58° C. and at a pressure sufficient to prevent the solvents from boiling, i.e., about 40 to 60 psig. To the top of the reactor through line 1 were fed 185 lb/hr of an HF solution containing 19 wt. % AcF and 15.2 wt. % HOAc, obtained, as shown in FIG. 2, as recycle streams from HF-removal column 20 and light ends column 30, and which form a continuous, dense HF-rich phase. As shown in FIG. 1, an IBB feed stream was fed through line 10, at a rate of 74 lb/hr to the bottom of the reactor, with flow to the middle of the reactor being blocked. A discontinuous light IBB-rich phase formed at the bottom of the reactor, which being less dense and largely insoluble in the continuous HF-rich phase, percolated to the top of the vessel. Reaction occurred between the AcF and possibly some of the HOAc as acetylating agent, and the IBB to form IBAP, which was extracted into the continuous HF-rich phase, and HF and possibly water, respectively, as by-product. IBB-rich phase containing reacted IBB collected at the top of the vessel and after phase separation, was recycled through line 5 and eventually line 10 as part of the IBB feed (which comprises both recycle IBB and makeup IBB) to the bottom of the vessel in an amount of 58.8 lb/hr. Fresh IBB in an amount of 15.2 lb/hr was continuously added through lines 6 and 10 to replace that used up in the reaction and dissolved in the HF-rich phase. From the bottom of extractor-reactor 3, 200 lb/hr of the HF-rich phase was removed containing, in addition to the HF in the feed stream and that formed as a by-product in the acetylation reaction, the desired product, IBAP, along with unreacted IBB, AcF, HOAc and other by-products. A sample of the exiting HF-rich stream withdrawn at P4 was treated to remove HF by quenching in ice water, neutralizing, and extracting with an organic solvent. After stripping away the solvent, the organic fraction remaining was found to contain 55.1 wt. % of IBAP and 37.5 wt. % of IBB. Analysis of a sample of IBB feed stream withdrawn at P3 indicated the presence of 0.3 wt. % of IBAP, 57.6 wt. % of IBB, and 1.8 wt. % of fluoride derived from HF and AcF.

The HF-rich product stream from extractor-reactor 3 was fed through line 12 to HF-removal column 20 containing 30 theoretical trays, where $Ac_2O$ was introduced to react with HF complexed with IBAP and HOAc and to form AcF, and light components primarily HF and AcF, were stripped overhead for recycle to extractor-reactor 3 through line 1, as referred to the first part of this example and described in U.S. Pat. No. 4,990,681. The HF-rich feed stream was fed near the top of column 30 at trays 26, 28 or 30. The $Ac_2O$ in an amount of 14 lb/hr was fed to column 20 below the feed point of the HF-rich feed stream, with a major proportion of $Ac_2O$ being fed at trays 20 or 24 and a minor proportion at trays 6, 9 or 14. A product stream in an amount 49 lb/hr was removed from the base of column 20 through line 26 and contained 26.9 wt. % of IBAP, 5.9 wt. % of IBB, 61.6 wt. % of HOAc, 2.1 wt. % of $Ac_2O$, and other by-products.

The product stream from HF removal column 20 was further purified by feeding it through line 26 to light ends distillation column 30 where the bulk of the HOAc was separated as an overhead stream from the IBAP product at a pressure of 10–50 mm Hg pressure. The overhead stream, suitable for recycle to extractor-reactor 3, was withdrawn through line 32 and condensed in line 33; it contained 88.1 wt. % of HOAc, 3.5 wt. % of $Ac_2O$ and 5.9 wt. % of IBB. The product stream in an amount of about 14.4 lb/hr was removed through line 31 and contained 91.6 wt. % of IBAP, with the bulk of the remainder being higher boiling by-products. The latter were substantially removed by further purification in a heavy ends distillation column.

EXAMPLE 2

The configuration of equipment was the same as in Example 1, but IBB was fed to the middle of the extractor-reactor instead of the bottom, so that the bottom part of the vessel acted as a "finishing zone" wherein additional residence time for the continuous HF-rich phase provided for further reaction between the acetylating agent, mostly AcF, and dissolved IBB in a homogeneous system, thus increasing the yield of IBAP. The temperature of the reactor was maintained at 60° C. To the top of the reactor through line 1 were fed 290 lb/hr of HF containing 6.8 wt. % AcF and 10.3 wt. % HOAc. IBB was fed through line 8 at a rate of 89 lb/hr to the middle of the reactor. 16.4 lb/hr of IBB were continuously added through line 6 to replace that used up in the reaction and dissolved in the HF-rich phase, and 307 lb/hr HF solution were removed from the bottom of the reactor through line 12. Analysis of the organic fraction of this stream as in Example 1 indicated 78.7 wt. % of IBAP and 13.3 wt. % of IBB, and analysis of a sample obtained from the middle of extractor-reactor 3 at P2 indicated 66.4 wt. % of IBAP and 27.7 wt. % of IBB.

The stream exiting from extractor-reactor 3 through line 12 was fed separately with 13 lb/hr of $Ac_2O$ to the thirty tray HF removal stripping column 20 as in Example 1. A solution was continuously withdrawn from the bottom of the column having a composition of 34.0 wt. % IBAP, 0.3 wt. % of IBB, 59.9 wt. % of HOAc, 3.0 wt. % of AcO and other by-products.

Separation of the HOAc from the crude acetylation product of HF removal column 20 was accomplished by distillation in light ends column 30 at 10–50 mm Hg pressure as in Example 1. The overhead stream from the distillation contained 94.8 wt. % of HOAc, 4.6 wt. % of $Ac_2O$, and 0.5 wt. % of IBB. A product stream composed of 92.2 wt. % of IBAP was continuously removed from the base of the column.

EXAMPLES 3 to 24

The procedure and equipment used to operate extractor-reactor 3 in these samples were similar to those of Examples 1 and 2 except that certain conditions such as feed stream rates and temperature were varied. Table I shows the rates of product withdrawn through line 12 ("Product Rate"), the IBB feed rate through lines 8 or 10 ("IBB Feed"), the HF and acetylating agent feed rate through line 1 ("HF Feed"), the IBB makeup rate through line 6 ("IBB Makeup"), the mode of operation ("Mode") with "1" indicating that IBB was fed to the middle of extractor-reactor 3 through line 8 as in Example 2, and "2" indicating that IBB was fed to the bottom of extractor-reactor 3 through line 10 as in Example 1, and the temperature of operation ("Temp").

TABLE I

| Example | Product Rate lb/hr | IBB* Feed lb/hr | HF Feed lb/hr | IBB Makeup lb/hr | Mode | Temp. °C. |
|---|---|---|---|---|---|---|
| 3  | 112 | 100 | 103 | 9.2  | 1 | 59.3 |
| 4  | 214 | 256 | 204 | 10.4 | 1 | 58.6 |
| 5  | 145 | 128 | 133 | 12.0 | 1 | 60.2 |
| 6  | 133 | 262 | 117 | 16.1 | 2 | 58.3 |
| 7  | 135 | 239 | 118 | 17.3 | 2 | 61.1 |
| 8  | 195 | 133 | 176 | 18.4 | 1 | 60.0 |
| 9  | 198 | 185 | 187 | 11.2 | 1 | 59.1 |
| 10 | 197 | 106 | 184 | 12.8 | 1 | 73.7 |
| 11 | 115 | 50  | 112 | 2.3  | 1 | 69.2 |
| 12 | 201 | 52  | 177 | 24.3 | 1 | 73.0 |
| 13 | 205 | 104 | 182 | 23.0 | 2 | 74.4 |
| 14 | 126 | 48  | 114 | 12.3 | 2 | 73.2 |
| 15 | 180 | 95  | 169 | 10.9 | 1 | 60.8 |
| 16 | 306 | 91  | 295 | 11.0 | 1 | 54.4 |
| 17 | 313 | 92  | 302 | 10.7 | 1 | 53.7 |
| 18 | 301 | 87  | 286 | 15.1 | 1 | 55.6 |
| 19 | 299 | 85  | 287 | 11.3 | 1 | 56.8 |
| 20 | 300 | 93  | 268 | 31.9 | 2 | 63.3 |
| 21 | 335 | 13  | 318 | 16.3 | 1 | 58.7 |
| 22 | 342 | 20  | 329 | 13.1 | 1 | 55.2 |
| 23 | 263 | 116 | 247 | 15.3 | 1 | 60.5 |
| 24 | 319 | 115 | 299 | 20.5 | 1 | 60.8 |

*Includes recycle IBB and makeup IBB

The compositions of various streams as indicated by the analyses of samples withdrawn at points P1, P2, P3 and P4 shown in FIG. 1, are given in Table II.

TABLE II

| | HF Feed, P1 | | Reactor Middle, P2 Organic Fraction | | Reactor Bottom P4 Organic Fraction | | IBB Feed, P3 | | |
|---|---|---|---|---|---|---|---|---|---|
| Example | [AcF] wt. % | [HoAc] wt. % | [IBAP] wt. % | [IBB] wt. % | [IBAP] wt. % | [IBB] wt. % | [IBAP] wt. % | [IBB] wt. % | [F] wt. % |
| 3   | 8.5  | 9.7  | 70.6 | 19.0 | 77.6 | 7.2  |      |      |     |
| 4   | 4.8  | 9.8  | 71.7 | 22.3 | 83.1 | 9.9  |      |      |     |
| 5   | 4.8  | 3.8  | 69.3 | 16.2 | 70.2 | 7.1  |      |      |     |
| 6   | 11.6 | 4.3  |      |      | 64.5 | 18.6 |      |      |     |
| 7   | 15.2 | 4.3  |      |      | 67.0 | 19.8 |      |      |     |
| 8   | 15.7 | 5.1  | 68.1 | 22.9 | 76.1 | 8.2  |      |      |     |
| 9   | 8.8  | 10.7 | 70.2 | 22.8 | 79.9 | 13.0 |      |      |     |
| 10* | 14.4 | 3.8  | 63.3 | 21.2 | 83.7 | 2.0  |      |      |     |
| 11  | 19.4 | 15.1 | 50.7 | 38.2 | 59.2 | 25.9 |      |      |     |
| 12  | 15.1 | 5.7  | 60.8 | 15.5 | 65.1 | 7.0  |      |      |     |
| 13  | 4.7  | 5.5  |      |      | 63.3 | 16.3 |      |      |     |
| 14  | 5.4  | 13.2 |      |      | 63.8 | 19.8 |      |      |     |
| 15  | 11.7 | 10.3 |      |      |      |      | 0.0  | 76.5 | 2.9 |
| 16  | 9.6  | 10.2 | 63.9 | 25.6 | 81.7 | 11.5 |      |      |     |
| 17  | 10.6 | 9.9  |      |      | 77.1 | 15.7 | 0.0  | 57.0 | 3.3 |
| 18  | 4.1  | 10.5 |      |      | 70.2 | 25.0 | 0.05 | 65.0 | 1.4 |
| 19  | 4.5  | 10.4 |      |      | 83.7 | 11.1 |      |      |     |
| 20  | 15.1 | 11.2 |      |      | 67.0 | 26.8 |      |      |     |
| 21  | 9.4  | 6.3  |      |      |      |      | 0.19 | 80.4 | 2.2 |
| 22  | #    | 6.1  | 78.5 | 17.0 | 88.7 | 6.4  |      |      |     |
| 23  | 6.8  | 10.1 | 49.6 | 44.1 | 81.5 | 11.8 |      |      |     |
| 24  | 9.3  | 8.4  | 61.2 | 31.1 | 75.5 | 15.3 |      |      |     |

*Analytical results show low accountability
Estimates to be 7 wt %

The results summarized in Table II of the examples carried out under mode 1, which provided for a finishing zone allowing for additional acetylation reaction between dissolved IBB and acetylating agent in homogenous system, indicate that the production stream leaving the bottom of the extractor-reactor always has a higher percentage of IBAP than the mixture entering the finishing zone at the middle of the extractor-reactor just below the IBB feed point. This demonstrates that significant additional acetylation of dissolved IBB does indeed occur in the finishing zone. Furthermore, a comparison of the results of the mode 1 examples with those carried out under mode 2, wherein no finishing zone was utilized, indicates that the product stream leaving the bottom of the extractor-reactor when it was operated in mode 1 tended in most cases to have a higher percentage of IBAP than was the case when the extractor-reactor was operated in mode 2. Thus, the utilization of a finishing zone or reactor is in most cases beneficial in providing for higher overall yields of IBAP.

Examples 21 and 22 above illustrate conditions wherein, referring to FIG. 1, the amount of aromatic compound-comprising feed flow through line 10 is equal to or nearly equal to the amount of fresh makeup aromatic compound-comprising feed through line 6. There is no significant recycle of aromatic compound from line 5 which proceeds from the top of the extractor-reactor. This occurs when the aromatic compound-containing phase is sufficiently reacted that an insignificant amount of aromatic compound remains to exit the top of the extractor-reactor. A review of the Example 21 data shows more makeup aromatic compound-comprising feed through line 6 than the sum of the aromatic compound-comprising recycle and makeup feed combined, a physical impossibility. This is attributed to flow measurement calibration errors or to the backup of recycle through line 5 into the top of the extractor-reactor.

It is preferable to react essentially all of the aromatic compound in a single pass through the extractor-reactor, since experimental data has shown that undesired isomers of the desired acylated or alkylated product tend to increase in amount (be more readily formed) when unreacted, aromatic compound is recycled.

EXAMPLE 25

An autoclave equipped with a window for observing HF solutions was charged with 61.2 g of acetic anhydride and 60 g of HF. The mixture was warmed to about 80° C. and molten 1,1,3, 4,4,6-hexamethyltetralin (HMT) was fed into the lower portion of the autoclave. A second phase was observed forming in the upper portion of the autoclave. After about ten (10) minutes, samples of each phase, in the upper and lower portions of the autoclave, were taken. The upper phase was comprised of unreacted HMT (about 33% by weight) and acylated product, 1,1,3,4,4,6-hexamethyl-7-acetyltetralin (HMAT) (about 2% by weight), with the remainder comprising HF and acetyl species. The lower phase was comprised of about 2% by weight HMT, about 2.5% by weight HMAT, with the remainder comprising HF and acetyl species. Although this autoclave example does not show the reactant-product separation obtained in the earlier examples, the phasing behavior exhibited can reasonably be expected to be useful in the reactor described in the preceding Examples.

EXAMPLE 26

This Example shows the limited solubility of p-cymene in HF, and indicates that p-cymene (methylisopropyl-benzene) can be acylated or alkylated using the process of the present invention.

An autoclave was charged with 26.8 g. of p-cymene and 150 g. of HF at about 0° C. The contents of the autoclave were stirred for about 5 minutes. Stirring was discontinued, and the phases formed within the autoclave were permitted to separate for about 30 minutes. A sample taken from the upper phase in the autoclave comprised about 93% by weight p-cymene and about 4% by weight HF. A sample taken from the lower phase in the autoclave comprised about 1% p-cymene and about 99% HF.

EXAMPLE 27

Alkylation reactions using HF as catalyst/solvent are also possible using the process of the present invention.

To illustrate the above, a mixture of 33.6 g. of 3,3-dimethyl-1-butene, 13.4 g. of p-cymene, and 100 g. of HF was reacted in a stirred autoclave at about $-40°$ C. for about 1 hour. The product mixture was transferred into ice/water, neutralized with KOH, and extracted using ethyl acetate. Removal of the ethylacetate extractant by rotary evacuation provided 36 g. of organic product which contained 19% by weight of the alkylated product, 1,1,3,4,4,6-hexamethyltetralin (HMT).

Alkylation agents which can be used in the process of the present invention are unsaturated $C_2$–$C_{20}$ alkyls, preferably unsaturated $C_2$–$C_{10}$ alkyls.

The scope of the present invention includes an embodiment wherein the aromatic compound provides the continuous phase and the HF-rich phase provides the discontinuous phase. Typically, the HF-rich phase migrates downward through the aromatic compound-comprising phase and collects in the bottom of the extractor-reactor for further processing in a manner similar to that described in the above preferred embodiments.

The scope of the present invention also includes an embodiment wherein the multistage reaction is carried out using concurrent flow of the aromatic compound-comprising phase with the HF-comprising phase. Concurrent flow can be achieved using, for example, a tubular reactor wherein a mixture comprising aromatic reactant, acetylating reagents and HF is fed into one end of the tubular reactor and the reaction takes place as the mixture proceeds under plug flow conditions along the length of the tube. The product mixture exiting the tubular reactor comprises unreacted aromatic reactant, hydrogen fluoride, product dissolved in hydrogen fluoride and unreacted acylating or alkylating agent. The product mixture can then be sent to a separation unit wherein the various components are separated using techniques of the kind described in U.S. Pat. No. 4,990,681.

The amount of aromatic reactant in the feed to the tubular reactor and/or the number of stages contained in the reactor can be adjusted so that no significant amount of aromatic reactant remains unreacted in the product mixture exiting the tubular reactor.

The embodiments described above are not intended to place undue limitations on the scope of the present invention, particularly regarding non-critical features of the invention, wherein one skilled in the art can make modifications and equivalent substitutions which provide obvious variations of the invention. Such variations are intended to fall within the scope of the present invention as defined in the following claims.

We claim:

1. A continuous process for the acylation of aromatic compounds in hydrogen fluoride, said process comprising the steps of:

(a) feeding liquid hydrogen fluoride and at least one acylation agent into an extractor-reactor to form a first, hydrogen-rich phase;
(b) feeding an aromatic compound-comprising material into said extractor-reactor to form a second, aromatic compound-rich phase; and
(c) contacting said first, hydrogen fluoride-rich phase with said second, aromatic compound-rich phase in a manner, within said extractor reactor, such that said acylation agent reacts with said aromatic compound to form an acylation product of said aromatic compound which is extracted into said hydrogen fluoride-rich phase wherein said acylation agent is selected from the group consisting of acetyl fluoride, a combination of acetic acid and acetyl fluoride, a combination of acetic anhydride and acetyl fluoride, and a combination of acetic acid, acetic ahyydride and acetyl fluoride, and said aromatic compound is selected from the group consisting of isobutylbenzene, methylisopropylbenzene, chlorobenzene, diphenyl, diphenylmethane, triphenylmethane, naphthalene, 2-methylnapthalene, tetralin, 1,1,3,4,4-6-hexamethyltetralin and phanthrene.

2. The process of claim 1, wherein at least a portion of said aromatic compound remains unreacted after step c), and wherein said unreacted aromatic compound is externally recycled, whereby said unreacted aromatic compound is used in combination with fresh aromatic compound to continue the reaction within said extractor-reactor.

3. The process of claim 1, wherein essentially all of said aromatic compound of said second phase is reacted after step c).

4. The process of claim 1, claim 2, or claim 3, wherein said aromatic compound is selected from the group consisting of isobutylbenzene; 1,1,3,4,4,6-hexamethyltetralin; and methylisopropylbenzene.

5. The process of claim 1, claim 2, or claim 3, wherein said hydrogen fluoride-rich phase is the continuous phase of said extractor-reactor reaction medium.

6. The process of claim 1, claim 2, or claim 3, wherein said aromatic compound-rich phase is the continuous phase of said extractor-reactor reaction medium.

* * * * *